United States Patent [19]
Cynshi et al.

[11] Patent Number: 6,103,753
[45] Date of Patent: *Aug. 15, 2000

[54] INTIMAL THICKENING INHIBITORY AGENT

[75] Inventors: Osamu Cynshi; Reiko Sekimori; Yoshiaki Kato, all of Shizuoka-ken, Japan

[73] Assignee: Chugai Seiyaku Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/068,610

[22] PCT Filed: Nov. 8, 1996

[86] PCT No.: PCT/JP96/03279

§ 371 Date: May 6, 1998

§ 102(e) Date: May 6, 1998

[87] PCT Pub. No.: WO97/17066

PCT Pub. Date: May 15, 1997

[30] Foreign Application Priority Data

Nov. 9, 1995 [JP] Japan ..................... 7-326166

[51] Int. Cl.$^7$ .................. A01N 43/12
[52] U.S. Cl. ........... 514/443; 514/446; 514/462; 514/469; 514/708; 514/709; 514/710; 514/711; 514/712; 514/713; 514/724; 514/728; 514/731; 514/733; 514/734; 514/736; 514/738; 514/739
[58] Field of Search ................ 514/443, 446, 514/462, 469, 708, 709, 710, 711, 712, 713, 724, 728, 731, 733, 734, 736, 738, 739

[56] References Cited

U.S. PATENT DOCUMENTS

| | | | |
|---|---|---|---|
| 5,326,757 | 7/1994 | Demopoulos | 514/167 |
| 5,480,888 | 1/1996 | Kodama et al. | 514/310 |
| 5,574,178 | 11/1996 | Tamura et al. | 549/562 |
| 5,789,436 | 8/1998 | Kato et al. | 514/443 |

FOREIGN PATENT DOCUMENTS

| | | |
|---|---|---|
| 5255084 | 10/1993 | Japan . |
| 6206842 | 7/1994 | Japan . |
| 7503010 | 3/1995 | Japan . |
| 095/27710 | 10/1995 | WIPO . |
| 9408930 | 3/1996 | WIPO . |

OTHER PUBLICATIONS

Ferns et al., Probucol inhibits neointimal thickening and macrophage accumulation after ballon injury in the cholesterol–fed rabbit, *Proc. Natl. Acad. Sci.*, 89:11312–11316, Dec. 1992.

Freyschuss et al., Antioxidant Treatment Inhibits the Development of Intimal Thickening after Ballon Injury of the Aorta in Hypercholesterolemic Rabbits, *J. Clin. Invest.*, 91:1282–1288, 1993.

Godfried et al., Potentiation of atherosclerotic lesion in rabbits by a high dietary level of vitamin E, *British Journal of Nutrition*, 61:607–617, 1989.

DeMaio et al., Vitamin E Supplementation, Plasma Lipids and Incidence of Restenosis After Percutaneous, Transluminal Coronary Angioplasty (PTCA), *Journal of the American College of Nutrition*, 11:68–73, 1992.

Schneider et al., Probucol Decreases Neointimal Formation in a Swine Model of Coronary Artery Ballon Injury, *Basic Science Report*, 88:628–637, 1993.

Konneh et al., Vitamin E inhibirs the intimal response to Balloon catheter injury in the carotid artery of the cholesterol–fed rat, *Antherosclerosis*, 113:29–39, 1995.

Lafont et al., Effect of Alpha–tocopherol on Restenosis after Angioplasty in a Model Experimental Atherosclerosis, *J. Clin. Invest.*, 95:1018–1025, 1995.

Tardif et al., Probucol and Multivitamins in the Prevention of Restenosis After Coronary Angioplasty, *he New England Journal of Medicine*, 320:365–372, 1997.

*Primary Examiner*—Frederick Krass
*Attorney, Agent, or Firm*—Browdy and Neimark

[57] ABSTRACT

An intimal thickening inhibitory agent comprising, as an active ingredient, a compound represented by formula (1):

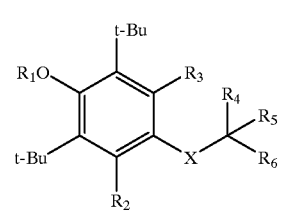

(1)

wherein X represents an oxygen atom or a group of formula (2):

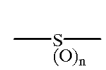

(2)

wherein n represents an integer of from 0 to 2, $R_1$ represents a hydrogen atom or an acyl group; $R_2$ represents a hydrogen atom, a lower alkyl group or a lower alkenyl group; $R_3$ represents a lower alkyl group; and $R_4$, $R_5$, and $R_6$, which may be the same or different, each represent a hydrogen atom or a substituted or unsubstituted alkyl group; or $R_3$ and $R_4$ may be taken together to form a 5-membered ring; or $R_5$ and $R_6$ may be taken together to form a cycloalkyl group; provided that $R_6$ is nil when $R_3$ and $R_4$ are taken together to form benzofuran or benzo[b]thiophene.

25 Claims, No Drawings

INTIMAL THICKENING INHIBITORY AGENT

This application is a 371 of PCT/JP96/03279, filed Nov. 8, 1996.

FIELD OF THE INVENTION

This invention relates to an intimal thickening inhibitory agent and more particularly an intimal thickening inhibitory agent comprising a 2,6-di-t-butylphenol derivative as an active ingredient.

BACKGROUND OF THE INVENTION

It is known that coronary sclerosis is a primary cause of ischemic heart diseases such as angina pectoris and cardiac infarction. Narrowing of the vascular lumen resulting from arteriosclerotic thickening of the intima brings about nutrition and oxygen deficiencies in the myocardial tissues to induce the above diseases. Percutaneous transluminal coronary angioplasty (hereinafter abbreviated as "PTCA") that has recently been developed as a treatment for the ischemic heart diseases such as angina pectoris and cardiac infarction is to physically dilate a blood vessel by inflating a balloon at the stenosis region of the coronary artery. However, the problem which has been recognized from the beginning of development of this treatment is that restenosis appears at the treated region within 3 to 6 months after the angioplasty at a frequency of about 40% (see Circulation, 77, pp. 361–371 (1988)).

Up to the present time, use of anticoagulants, antiplatelet agents or drugs having an inhibitory effect on proliferation of vascular smooth muscle cells has been attempted to prevent stenosis due to arteriosclerotic intimal thickening or restenosis after PTCA. Thus, an extensive research for such drug has been conducted (see, for example, JP 2-121922 A/90, JP 3-83923 A/91, JP 3-118383 A/91, JP 4-99775 A/92, JP 4-154720 A/92, JP 6-135829 A/94, JP 6-206842 A/94, JP 7-25768 A/95, JP 7-149641 A/95 and JP 7-223958 A/95). However, there has been found no drug having clinically sufficient inhibitory effect on vascular stenosis due to arteriosclerotic intimal thickening or restenosis due to intimal thickening after PTCA (see, *Nihon Rinsyo,* 52 (extra ed.), pp. 869–872 (1994)).

DISCLOSURE OF THE INVENTION

As a result of an extensive research in an attempt to solve the foregoing problem, it has been found that a compound represented by formula (1):

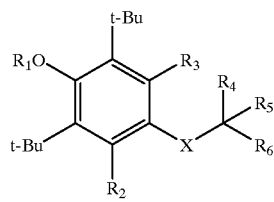

wherein X represents an oxygen atom or a group of formula (2);

wherein n represents an integer of from 0 to 2;

$R_1$ represents a hydrogen atom or an acyl group;

$R_2$ represents a hydrogen atom, a lower alkyl group or a lower alkenyl group;

$R_3$ represents a lower alkyl group; and $R_4$, $R_5$, and $R_6$, which may be the same or different, each represent a hydrogen atom, a substituted or unsubstituted alkyl group, a substituted or unsubstituted alkenyl group, a substituted or unsubstituted alkynyl group, or a substituted or unsubstituted aryl group; or $R_3$ and $R_4$ may be taken together to form a 5-membered ring; or $R_5$ and $R_6$ may be taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzofuran ring, a benzo[b]thiophene ring, a benzo[b]thiophene-1-oxide ring or a benzo[b]thiophene-1,1-dioxide ring, exhibits an excellent inhibitory effect on proliferation of vascular smooth muscle cells as well as on intimal thickening in balloon injury models.

The fact that the compound represented by formula (1) is effective in the treatment and prevention of ischemic organopathy such as arteriosclerosis, cardiac infarction and apoplexy has already been revealed (see JP 6-206842 A/94, WO 94-08930, and WO 95-27710).

BEST MODE FOR CARRYING OUT THE INVENTION

In the above formula (1), the acyl groups include an acetyl group, a formyl group, a propionyl group, a benzoyl group, a benzyloxycarbonyl group, an aminoacetyl group, an N-methylaminoacetyl group, and an N,N-dimethylaminoacetyl group. The term "lower alkyl group" means a straight- or branched-chain alkyl group having 1 to 6 carbon atoms, for example, a methyl group, an ethyl group, a n-propyl group, an i-propyl group, a n-butyl group, a sec-butyl group, and a tert-butyl group. The term "lower alkenyl group" means a straight- or branched-chain alkenyl group having 2 to 6 carbon atoms, for example, a vinyl group, an allyl group, a butenyl group, and a pentenyl group.

The alkyl group represented by $R_4$, $R_5$, or $R_6$ is a straight- or branched-chain alkyl group having 1 to 20 carbon atoms, for example, a methyl group, an ethyl group, a n-propyl group, an i-propyl group, a n-butyl group, a sec-butyl group, a tert-butyl group, a pentyl group, a hexyl group, a heptyl group, an octyl group, a nonyl group, and a decyl group. The alkenyl group is a straight- or branched-chain alkenyl group having 2 to 20 carbon atoms, for example, a vinyl group, an allyl group, a butenyl group, a pentenyl group, a geranyl group, and a farnesyl group. The alkynyl group is a straight- or branched-chain alkynyl group having 2 to 20 carbon atoms, for example, an ethynyl group, a propynyl group, and a butynyl group. The aryl group is a monovalent substituent derived from an aromatic hydrocarbon by removing one hydrogen atom, for example, a phenyl group, a tolyl group, a xylyl group, a biphenyl group, a naphthyl group, an anthryl group, and a phenanthryl group. Substituents in the substituted alkyl, alkenyl, alkynyl or aryl group include a halogen atom, a lower alkyl group, a hydroxyl group, an amino group, an alkoxy group, an aryloxy group, a nitro group, and a trifluoromethyl group.

The 5-membered rings formed by $R_3$ and $R_4$ include a furan ring, a dihydrofuran ring, a thiophene ring, and a dihydrothiophene ring, which are taken together with the benzene ring to form a benzofuran ring, a dihydrobenzofuran ring, a benzo[b]thiophene ring, and a dihydrobenzothiophene ring, respectively.

The cycloalkyl group is a cycloalkyl group having 3 to 8 carbon atoms, for example, a cyclopropyl group, a cyclobutyl group, a cyclopentyl group, a cyclohexyl group, a cycloheptyl group, and a cyclooctyl group. The heterocyclic rings derived from the cycloalkyl group by substituting any one or more methylene groups on the ring with oxygen atoms, sulfur atoms or alkyl-substituted nitrogen atoms include, for example, a tetrahydropyranyl group.

Where X in formula (1) is an oxygen atom, $R_1$ is preferably a hydrogen atom, an acetyl group, a benzyloxycarbonyl group, an aminoacetyl group, an N-methylaminoacetyl group or an N,N-dimethylaminoacetyl group, particularly a hydrogen atom, an acetyl group or an N,N-dimethylaminoacetyl group;

$R_2$ is preferably a hydrogen atom, a methyl group or a n-propyl group, particularly a hydrogen atom;

$R_3$ and $R_4$ are preferably taken together to form a furan ring or a dihydrofuran ring, particularly a dihydrofuran ring;

$R_5$ is preferably a hydrogen atom, a methyl group, a n-butyl group, a n-pentyl group, a n-hexyl group or an i-amyl group, particularly a n-pentyl group; and $R_6$ is preferably a hydrogen atom, a methyl group, a n-butyl group, a n-pentyl group, a n-hexyl group or an i-amyl group, particularly a n-pentyl group; or $R_5$ and $R_6$ are preferably taken together to form a cyclopentyl group, a cyclohexyl group, a cycloheptyl group, a cyclooctyl group, or a tetrahydropyranyl group, particularly a cyclohexyl group, a cycloheptyl group, or a cyclooctyl group.

Where X in formula (1) is a group represented by formula (2):

$$-\underset{(O)_n}{S}-\qquad(2)$$

wherein n is an integer of from 0 to 2, $R_1$ is preferably a hydrogen atom, an acetyl group, a benzyloxycarbonyl group, an aminoacetyl group, an N-methylaminoacetyl group or an N,N-dimethylaminoacetyl group, particularly a hydrogen atom, an acetyl group or an N,N-dimethylaminoacetyl group;

$R_2$ is preferably a hydrogen atom, a methyl group or an n-propyl group, particularly a hydrogen atom;

$R_3$ and $R_4$ are preferably taken together to form a thiophene ring or a dihydrothiophene ring, particularly a dihydrothiophene ring;

$R_5$ is preferably a hydrogen atom, a methyl group, a n-butyl group, a n-pentyl group, a n-hexyl group or an i-amyl group, particularly a n-pentyl group; and $R_6$ is preferably a hydrogen atom, a methyl group, a n-butyl group, a n-pentyl group, a n-hexyl group or an i-amyl group, particularly a n-pentyl group; or $R_5$ and $R_6$ are preferably taken together to form a cyclopentyl group, a cyclohexyl group, a cycloheptyl group, a cyclooctyl group, or a tetrahydropyranyl group, particularly a cyclohexyl group, a cycloheptyl group, or a cyclooctyl group; and n is preferably 0 or 1, particularly 0.

Examples of the specific compounds used for the inhibitory agent of the present invention include 4,6-di-t-butyl-5-hydroxy-2,3-dihydrobenzofuran, 4,6-di-t-butyl-5-hydroxy-2-methyl-2,3-dihydrobenzofuran, 4,6-di-t-butyl-5-hydroxy-2,2-dimethyl-2,3-dihydrobenzofuran, 4,6-di-t-butyl-2,2-diethyl-5-hydroxy-2,3-dihydrobenzofuran, 4,6-di-t-butyl-2,2-di-n-propyl-5-hydroxy-2,3-dihydrobenzofuran, 4,6-di-t-butyl-2,2-di-n-butyl-5-hydroxy-2,3-dihydrobenzofuran, 4,6-di-t-butyl-5-hydroxy-2-octylbenzofuran, 4,6-di-t-butyl-5-hydroxy-2-octyl-2,3-dihydrobenzofuran, 2,4,6-tri-t-butyl-5-hydroxy-2,3-dihydrobenzofuran, 4,6-di-t-butyl-2,2-di-i-propyl-5-hydroxy-2,3-dihydrobenzofuran, 4,6-di-t-butyl-2,2-diphenyl-5-hydroxy-2,3-dihydrobenzofuran, 4,6-di-t-butyl-2,2-dibenzyl-5-hydroxy-2,3-dihydrobenzofuran, 4,6-di-t-butyl-2-chloromethyl-5-hydroxy-2,3-dihydrobenzofuran, 4,6-di-t-butyl-5-hydroxy-2,3-dihydrobenzofuran-2-spiro-1'-cyclopentane, 4,6-di-t-butyl-5-hydroxy-2,3-dihydrobenzofuran-2-spiro-1'-cyclohexane, 4,6-di-t-butyl-5-hydroxy-2,3-dihydrobenzofuran-2-spiro-1'-cycloheptane, 4,6-di-t-butyl-5-hydroxy-2,3-dihydrobenzofuran-2-spiro-1'-cyclooctane, 4,6-di-t-butyl-5-hydroxy-2,3-dihydrobenzofuran-2-spiro-4'-tetrahydropyran, 5-hydroxy-4,6-di-t-butyl-2,2-dimethyl-7-propyl-2,3-dihydrobenzofuran, 4,6-di-t-butyl-5-hydroxybenzofuran, 4,6-di-t-butyl-5-hydroxy-2-methylbenzofuran, 2,4,6-tri-t-butyl-5-hydroxybenzofuran, 2,6-di-t-butyl-3-methyl-4-propyloxyphenol, 4-allyloxy-2,6-di-t-butyl-3-methylphenol, 1,3-bis(3,5-di-t-butyl-4-hydroxy-2-methylphenoxy)propane, 4,6-di-t-butyl-2,2-di-n-pentyl-5-hydroxy-2,3-dihydrobenzofuran, 4,6-di-t-butyl-2,2-di-n-octyl-5-hydroxy-2,3-dihydrobenzofuran, 4,6-di-t-butyl-2,2-di-n-heptyl-5-hydroxy-2,3-dihydrobenzofuran, 4,6-di-t-butyl-2,2-di-n-hexyl-5-hydroxy-2,3-dihydrobenzofuran, 2,2-di-i-amyl-4,6-di-t-butyl-5-hydroxy-2,3-dihydrobenzofuran, 4,6-di-t-butyl-5-hydroxy-2-methyl-2-(4,8,12-trimethyltrideco trideca-3(E),7(E),11-trienyl)-2,3-dihydrobenzofuran, 4,6-di-t-butyl-5-hydroxy-2-methyl-2-(4',8',12'-trimethyltridecyl)-2,3-dihydrobenzofuran, 4,6-di-t-butyl-5-hydroxy-2-(5-hydroxy-4-methyl-3(E)-pentenyl)-2-methyl-2,3-dihydrobenzofuran, 4,6-di-t-butyl-5-hydroxy-2-hydroxymethyl-2-methyl-2,3-dihydrobenzofuran, 4,6-di-t-butyl-5-hydroxy-2,2-di-n-pentyl-2,3-dihydrobenzothiophene, 4,6-di-t-butyl-5-hydroxy-2-methyl-2,3-dihydrobenzothiophene, 4,6-di-t-butyl-5-hydroxy-2,2-dimethyl-2,3-dihydrobenzothiophene, 4,6-di-t-butyl-5-hydroxybenzo[b]thiophene, 4,6-di-t-butyl-5-hydroxy-2,3-dihydrobenzothiophene, 4,6-di-t-butyl-5-hydroxy-2,2-diethyl-2,3-dihydrobenzothiophene, 4,6-di-t-butyl-5-hydroxy-2,2-di-n-propyl-2,3-dihydrobenzothiophene, 4,6-di-t-butyl-5-hydroxy-2,2-di-i-propyl-2,3-dihydrobenzothiophene, 4,6-di-t-butyl-5-hydroxy-2,2-di-n-butyl-2,3-dihydrobenzothiophene, 4,6-di-t-butyl-5-hydroxy-2,2-di-i-amyl-2,3-dihydrobenzothiophene, 4,6-di-t-butyl-5-hydroxy-2,2-di-n-hexyl-2,3-dihydrobenzothiophene, 4,6-di-t-butyl-5-hydroxy-2,2-di-n-heptyl-2,3-dihydrobenzothiophene, 4,6-di-t-butyl-5-hydroxy-2,2-di-n-octyl-2,3-dihydrobenzothiophene, 4,6-di-t-butyl-5-hydroxy-2,2-diphenyl-2,3-dihydrobenzothiophene, 4,6-di-t-butyl-5-hydroxy-2,2-dibenzyl-2,3-dihydrobenzothiophene, 4,6-di-t-butyl-5-hydroxy-2-methyl-2-(4,8,12-trimethyltrideca-3(E), 7(E),11-trienyl)-2,3-dihydrobenzothiophene, 4,6-di-t-butyl-5-hydroxy-2-methyl-2-(4,8,12-trimethyltridecyl)-2,3-dihydrobenzothiophene, 4,6-di-t-butyl-5-hydroxy-2-n-octyl-2,3-dihydrobenzothiophene, 2,4,6-tri-t-butyl-5-hydroxy-2,3-dihydrobenzothiophene, 4,6-di-t-butyl-5-hydroxy-2,2-dimethyl-7-n-propyl-2,3-dihydrobenzothiophene, 4,6-di-t-butyl-5-hydroxy-2,3-dihydrobenzothiophene-2-spiro-1'-cyclopentane, 4,6-di-t-butyl-5-hydroxy-2,3-dihydrobenzothiophene-2-spiro-1'-cyclohexane, 4,6-di-t-butyl-5-hydroxy-2,3-dihydrobenzothiophene-2-spiro-1'-cycloheptane, 4,6-di-t-butyl-5-hydroxy-2,3-dihydrobenzothiophene-2-spiro-1'-cyclooctane, 4,6-di-t-butyl-2-methyl-5-hydroxybenzo[b]thiophene, 2,4,6-tri-t-butyl-5-hydroxybenzo[b]thiophene, 4,6-di-t-butyl-2-octyl-5-hydroxybenzo[b]thiophene, 4,6-di-t-butyl-5-hydroxy-2-(N,N-dimethylaminomethyl)-2-methyl-2,3-dihydrobenzothiophene, 4,6-di-t-butyl-5-hydroxy-2-hydroxymethyl-2-methyl-2,3-dihydrobenzothiophene, 4,6-di-t-butyl-5-hydroxy-2-methyl-2-(4,8-dimethylnona-3(E),7-dienyl)-2,3-dihydrobenzothiophene, and 4,6-di-t-butyl-5-hydroxy-2-methyl-2-(4,8-dimethylnonyl)-2,3-dihydrobenzothiophene.

The compound represented by formula (1) used in the present invention is synthesized in accordance with, for example, the process described in JP 6-206842 A/94 or WO 95-27710.

The vascular intimal thickening inhibitory agent of the present invention can be used in the form of a pharmaceutical composition comprising a compound of formula (1) together with physiologically non-toxic solid or liquid pharmaceutical carrier. The pharmaceutical composition may be in a variety of dosage forms depending on the administration route. Suitable dosage forms include tablets, granules, pills, capsules, solutions, syrups, suspensions, emulsions, and injection solutions. Usual pharmaceutical carriers, such as excipient, binder, disintegrant, lubricant, coating agent, solubilizer, emulsifier, suspending agent, stabilizer, and solvents, may be used.

The compound represented by formula (1) and the above pharmaceutical composition according to the present invention can be administered by an oral or parenteral route such as intravenous injection or as a sustained release formulation or by a topical route, such as through a catheter.

The actual dosage of the compound of formula (1) to be required for inhibiting restenosis after PTCA depends on the age of the patient, the severity of the condition to be treated, the administration route, and the like. However, the effective dosage which is generally accepted will be in the range of, for example, 1 to 1000 mg, preferably 100 to 300 mg per day in the treatment of adult human. The dosage is preferably given in 1 to 3 dose administrations daily to the patient in need of such treatment.

EXAMPLES

The present invention will now be illustrated with reference to the following Examples, but it should be understood that the present invention is not construed as being limited thereto.

The compounds of Examples 1 to 46 were synthesized in accordance with the process described in JP 6-206842 A/94.

Example 1

4,6-Di-t-butyl-5-hydroxy-2,3-dihydrobenzofuran

Example 2

4,6-Di-t-butyl-5-hydroxy-2-methyl-2,3-dihydrobenzofuran

Example 3

5-Acetoxy-4,6-di-t-butyl-2,2-dimethyl-2,3-dihydrobenzofuran

Example 4

4,6-Di-t-butyl-5-hydroxy-2,2-dimethyl-2,3-dihydrobenzofuran

Example 5

5-Acetoxy-4,6-di-t-butyl-2,2-diethyl-2,3-dihydrobenzofuran

Example 6

4,6-Di-t-butyl-2,2-diethyl-5-hydroxy-2,3-dihydrobenzofuran

Example 7

4,6-Di-t-butyl-2,2-di-n-propyl-5-hydroxy-2,3-dihydrobenzofuran

Example 8

4,6-Di-t-butyl-2,2-di-n-butyl-5-hydroxy-2,3-dihydrobenzofuran

Example 9

5-Acetoxy-4,6-di-t-butyl-2-(1-octenyl)benzofuran

Example 10

5-Acetoxy-4,6-di-t-butyl-2-octylbenzofuran

Example 11

4,6-Di-t-butyl-5-hydroxy-2-octylbenzofuran

Example 12

4,6-Di-t-butyl-5-hydroxy-2-octyl-2,3-dihydrobenzofuran

Example 13

2,4,6-Tri-t-butyl-5-hydroxy-2,3-dihydrobenzofuran

Example 14

4,6-Di-t-butyl-2,2-di-i-propyl-5-hydroxy-2,3-dihydrobenzofuran

Example 15

4,6-Di-t-butyl-2,2-diphenyl-5-hydroxy-2,3-dihydrobenzofuran

Example 16

4,6-Di-t-butyl-2,2-dibenzyl-5-hydroxy-2,3-dihydrobenzofuran

Example 17

4,6-Di-t-butyl-2-chloromethyl-5-hydroxy-2,3-dihydrobenzofuran

Example 18

4,6-Di-t-butyl-5-hydroxy-2,3-dihydrobenzofuran-2-spiro-1'-cyclopentane

Example 19

4,6-Di-t-butyl-5-hydroxy-2,3-dihydrobenzofuran-2-spiro-1'-cyclohexane

Example 20

4,6-Di-t-butyl-5-hydroxy-2,3-dihydrobenzofuran-2-spiro-1'-cycloheptane

Example 21

4,6-Di-t-butyl-5-hydroxy-2,3-dihydrobenzofuran-2-spiro-1'-cyclooctane

Example 22

4,6-Di-t-butyl-5-hydroxy-2,3-dihydrobenzofuran-2-spiro-4'-tetrahydropyran

Example 23

4-Acetoxy-3,5-di-t-butyl-1-(2-methyl-2-propenyloxy)-2-propylbenzene

Example 24

5-Acetoxy-4,6-di-t-butyl-2,2-dimethyl-7-propyl-2,3-dihydrobenzofuran

Example 25

5-Hydroxy-4,6-di-t-butyl-2,2-dimethyl-7-propyl- 2,3-dihydrobenzofuran

Example 26

5-Acetoxy-4,6-di-t-butylbenzofuran

Example 27

4,6-Di-t-butyl-5-hydroxybenzofuran

Example 28

4,6-Di-t-butyl-5-hydroxy-2-methylbenzofuran

Example 29

2,4,6-Tri-t-butyl-5-hydroxybenzofuran

Example 30

1-Acetoxy-2,6-di-t-butyl-3-methyl-4-propyloxybenzene

Example 31

2,6-Di-t-butyl-3-methyl-4-propyloxyphenol

Example 32

1-Acetoxy-4-allyloxy-2,6-di-t-butyl-3-methylbenzene

Example 33

4-Allyloxy-2,6-di-t-butyl-3-methylphenol

Example 34

1,3-Bis(4-acetoxy-3,5-di-t-butyl-2-methylphenoxy)propane

Example 35

1,3-Bis(3,5-di-t-butyl-4-hydroxy-2-methylphenoxy)propane

Example 36

4,6-Di-t-butyl-2,2-di-n-pentyl-5-hydroxy-2,3-dihydrobenzofuran

Example 37

4,6-Di-t-butyl-2,2-di-n-octyl-5-hydroxy-2,3-dihydrobenzofuran

Example 38

4,6-Di-t-butyl-2,2-di-n-heptyl-5-hydroxy-2,3-dihydrobenzofuran

Example 39

4,6-Di-t-butyl-2,2-di-n-hexyl-5-hydroxy-2,3-dihydrobenzofuran

Example 40

5-Acetoxy-2,2-di-i-amyl-4,6-di-t-butyl-2,3-dihydrobenzofuran

Example 41

2,2-Di-i-amyl-4,6-di-t-butyl-5-hydroxy-2,3-dihydrobenzofuran

Example 42

5-Acetoxy-4,6-di-t-butyl-2-methyl-2-(4,8,12-trimethylyltrideca-3(E),7(E),11-trienyl)-2,3-dihydrobenzofuran

Example 43

4,6-Di-t-butyl-5-hydroxy-2-methyl-2-(4,8,12-trimethyltrideca-3(E),7(E),11-trienyl)-2,3-dihydrobenzofuran

Example 44

4,6-Di-t-butyl-5-hydroxy-2-methyl-2-(4',8',12'-trimethyltridecyl)-2,3-dihydrobenzofuran

Example 45

5-Acetoxy-4,6-di-t-butyl-2-(5-hydroxy-4-methyl-3(E)-pentenyl)-2-methyl-2,3-dihydrobenzofuran

Example 46

4,6-Di-t-butyl-5-hydroxy-2-(5-hydroxy-4-methyl-3(E)-pentenyl)-2-methyl-2,3-dihydrobenzofuran

Example 47

5-Acetoxy-4,6-di-t-butyl-2-hydroxymethyl-2-methyl-2,3-dihydrobenzofuran

In 200 ml of chloroform was dissolved 10.0 g of 4-acetoxy-3,5-di-t-butyl-2-(2-methyl-2-propenyl)phenol synthesized in accordance with JP 6-206842 A/94, and 11.0 g of m-chloroperbenzoic acid was added thereto, followed by heating under reflux for one day. After cooling, a saturated aqueous solution of sodium thiosulfate was added to the reaction mixture, and the mixture was extracted with chloroform. The organic layer was washed with a saturated sodium chloride aqueous solution, dried over anhydrous magnesium sulfate, and concentrated. The residue was purified by silica gel column chromatography (25% ethyl acetate in n-hexane) to give 7.3 g (yield: 70%) of 5-acetoxy-4,6-di-t-butyl-2-hydroxymethyl-2-methyl-2,3-dihydrobenzofuran (rotational isomer mixture) as a colorless oil.

$^1$H-NMR (270 MHz, CDCl$_3$) δ ppm: 1.30 (s, 9H), 1.37 (s, 9H), 1.38 (s, 1.5H), 1.45 (s, 1.5H), 2.30 (s, 3H), 3.06 (d, 0.5H, J=15.5 Hz), 3.16 (d, 0.5H, J=15.5 Hz), 3.38 (d, 0.5H, J=15.5 Hz), 3.52 (d, 0.5H, J=15.5 Hz), 3.58–3.72 (m, 2H), 6.75 (s, 0.5H), 6.76 (s, 0.5H).

Mass: 334 (M$^+$)

Example 48

4,6-Di-t-butyl-5-hydroxy-2-hydroxymethyl-2-methyl-2,3-dihydrobenzofuran

A solution of 500 mg of 5-acetoxy-4,6-di-t-butyl-2-hydroxymethyl-2-methyl-2,3-dihydrobenzofuran in 7 ml of tetrahydrofuran was added dropwise to a suspension of 114 mg of lithium aluminum hydride in 3 ml of tetrahydrofuran under nitrogen atmosphere. The reaction mixture was heated under reflux for 2 hours. After allowing the mixture to attain room temperature, ethyl acetate was added dropwise, 10% hydrochloric acid was added thereto, and the mixture was extracted with ethyl acetate. The organic layer was dried over anhydrous magnesium sulfate and concentrated. The residue was purified by silica gel column chromatography (20% ethyl acetate in n-hexane) to yield 320 mg (73%) of 4,6-di-t-butyl-5-hydroxy-2-hydroxymethyl-2-methyl-2,3-dihydrobenzofuran as a white solid.

Melting point: 126–128° C.

$^1$H-NMR (270 MHz, CDCl$_3$) δ ppm: 1.38 (s, 3H), 1.40 (s, 9H), 1.49 (s, 9H), 2.04 (bs, 1H), 3.14 (d, 1H, J=15.5 Hz), 3.45 (d, 1H, J=15.5 Hz), 3.59 (d, 2H, J=1.65 Hz), 4.74 (s, 1H), 6.65 (s, 1H).

IR (cm$^{-1}$): 3648, 3448, 2960

Mass: 292 (M$^+$)

The compounds of Examples 49 to 67 were synthesized according to the process described in WO 95-27710.

Example 49

5-Acetoxy-4,6-di-t-butyl-2,2-di-n-pentyl-2,3-dihydrobenzothiophene

Example 50

4,6-Di-t-butyl-5-hydroxy-2,2-di-n-pentyl-2,3-dihydrobenzothiophene

Example 51

4,6-Di-t-butyl-5-hydroxy-2-methyl-2,3-dihydrobenzothiophene

Example 52

4,6-Di-t-butyl-5-hydroxy-2,2-dimethyl-2,3-dihydrobenzothiophene

Example 53

5-Acetoxy-4,6-di-t-butylbenzo[b]thiophene

Example 54

4,6-Di-t-butyl-5-hydroxybenzo[b]thiophene

Example 55

5-Acetoxy-4,6-di-t-butylbenzo[b]thiophene-1,1-dioxide

Example 56

5-Acetoxy-4,6-di-t-butyl-2,3-dihydrobenzothiophene-1,1-dioxide

Example 57

4,6-Di-t-butyl-5-hydroxy-2,3-dihydrobenzothiophene

Example 58

4,6-Di-t-butyl-5-hydroxy-2,3-dihydrobenzothiophene-2-spiro-1'-cyclohexane

Example 59

5-Acetoxy-4,6-di-t-butyl-2-iodomethyl-2-methyl-2,3-dihydrobenzothiophene

Example 60

5-Acetoxy-4,6-di-t-butyl-2-(N,N-dimethylaminomethyl)-2-methyl-2,3-dihydrobenzothiophene

Example 61

4,6-Di-t-butyl-5-hydroxy-2-(N,N-dimethylaminomethyl)-2-methyl-2,3-dihydrobenzothiophene

Example 62

5-Acetoxy-2-acetoxymethyl-4,6-di-t-butyl-2-methyl-2,3-dihydrobenzothiophene

Example 63

4,6-Di-t-butyl-5-hydroxy-2-hydroxymethyl-2-methyl-2,3-dihydrobenzothiophene

Example 64

4,6-Di-t-butyl-5-hydroxy-2-methyl-2-(4,8-dimethylnona-3(E),7-dienyl)-2,3-dihydrobenzothiophene

Example 65

4,6-Di-t-butyl-5-hydroxy-2-methyl-2-(4,8-dimethylnonyl)-2,3-dihydrobenzothiophene

Example 66

4,6-Di-t-butyl-5-hydroxy-2-methyl-2-(4,8,12-trimethyl-trideca-3(E),7(E),11-trienyl)-2,3-dihydrobenzothiophene

Example 67

4,6-Di-t-butyl-5-hydroxy-2-methyl-2-(4,8,12-trimethyltridecyl)-2,3-dihydrobenzothiophene

Test Example 1

Inhibitory Effect on Proliferation of Vascular Smooth Muscle Cells (in vitro)

In order to assess the inhibitory effect of a compound of the present invention on serum-stimulated proliferation of vascular smooth muscle cells in vitro, the compound obtained in Example 36 was tested using A7r5 cells derived from the aorta of a rat (ATCC-CRL-1444).

Using DMEM medium containing 10% FBS, the cells were placed on 96-well microtiter plates with 5×10$^3$ cells/0.2 ml/well and then incubated. The medium was exchanged for 2% FBS-containing DMEM medium on the third day and then for 0.2% FBS-containing DMEM medium on the fourth day from the start of the incubation. After 48-hour incubation in the 0.2% FBS-containing DMEM medium, the medium was removed, 0.1 ml of DMEM medium and the test compound were added, and the cells were stimulated with serum (2% FBS) to proliferate. The test compound was added to the wells in the form of a solution or suspension in ethanol in an amount of 0.5 μl/well to final compound concentrations indicated in Table 1 below and the resultant ethanol concentration of 0.5% in each well. BrdU was pulsed to the wells from the 16th to 38th hours or from the 38th to 64th hours after the stimulation to a final concentration of 10 μM, and the uptake of BrdU into DNA was evaluated as an indication of cell proliferation. The BrdU uptake was measured by means of an EIA kit containing an anti-BrdU antibody (5-Bromo-2'-deoxy-uridine Labeling and Detection Kit III, available from Bohringer Mannheim Biochemica). The results obtained are shown in Table 1 below.

TABLE 1

Inhibitory Effect on Proliferation
of Vascular Smooth Muscle Cells (1)

| | Concn. | Absorbance (difference between 405 nm and 492 nm) | |
|---|---|---|---|
| | ($\mu$M) | 16–38 hrs. | 38–64 hrs. |
| Control | | 0.433 ± 0.008 | 0.436 ± 0.060 |
| Example 36 | 10 | 0.397 ± 0.054 | 0.195 ± 0.017 |
| Example 36 | 30 | 0.362 ± 0.026 | 0.085 ± 0.006 |
| Example 36 | 100 | 0.290 ± 0.031 | 0.049 ± 0.006 | n = 3;
Mean ± Standard Deviation

As is shown in Table 1, the compound of Example 36 inhibits the serum-stimulated proliferation of vascular smooth muscle cells dose-dependently.

Test Example 2

Inhibitory Effect on Proliferation of Vascular Smooth Muscle Cells (in vitro)

In order to assess the inhibitory effect of a compound of the present invention on serum- or PDGF-stimulated proliferation of vascular smooth muscle cells in vitro, the compound obtained in Example 36 was tested using A7r5 cells derived from the aorta of a rat (ATCC-CRL-1444). Further, the effect was compared with that of α-tocopherol which was reported to have an inhibitory effect on proliferation of vascular smooth muscle cells (see *J. Biol. Chem.*, 266, pp. 6188–6194 (1991)).

Using DMEM medium containing 10% FBS, the cells were placed on 96-well microtiter plates with 5×10$^3$ cells/0.2 ml/well and then incubated. The medium was exchanged for 2% FBS-containing DMEM medium on the third day and then for 0.2% FBS-containing DMEM medium on the fourth day from the start of the incubation. After 48-hour incubation in the 0.2% FBS-containing DMEM medium, the medium was removed, 0.2 ml of DMEM medium and the test compound were added, and the cells were stimulated with serum (2% FBS) or PDGF (PDGF-BB: human origin, available from Becton Dickinson Labware) (4 ng/ml) to proliferate. The test compound was added to the wells in the form of a solution or suspension in ethanol in amount of 1 $\mu$l/well to final compound concentrations indicated in Table 2 below and the resultant ethanol concentration of 0.5% in each well. Eight hours after the stimulation, hydroxyurea was added to a final concentration of 1.5 mM to synchronize the cell cycle strictly. After additional 14-hour incubation, the medium containing hydroxyurea was removed and the cells were washed, and DMEM medium, the test compound and the proliferation stimulator were added thereto again. Further, [$^3$H]-thymidine (1 $\mu$Ci/well; 20 $\mu$Ci/mmol; available from NEN Research) was added. The [$^3$H]-thymidine uptake in 5 hours was measured as an indication of cell proliferation. The results obtained are shown in Table 2 below.

TABLE 2

Inhibitory Effect on Proliferation
of Vascular Smooth Muscle Cells (2)

| | | Count by Liquid Scintillation Counter | |
|---|---|---|---|
| | Concn. ($\mu$M) | FBS Stimulation (CPM) | PDGF Stimulation (CPM) |
| Control | | 42789 ± 1063 | 24517 ± 2370 |
| α-Tocopherol | 30 | 28058 ± 3912 | 12493 ± 2978 |
| α-Tocopherol | 100 | 25706 ± 4160 | 12159 ± 2362 |
| Example 36 | 100 | 14147 ± 1372 | 7881 ± 356 | n = 3;
Mean ± Standard Deviation

As shown in Table 2 above, the compound of Example 36 inhibits serum- or PDGF-stimulated proliferation of vascular smooth muscle cells. The inhibitory effect of the compound is higher than that of a-tocopherol.

Test Example 3

Inhibitory Effect on Proliferation of Vascular Smooth Muscle Cells (in vitro)

In order to assess the inhibitory effect of the compounds of the present invention on serum-stimulated proliferation of vascular smooth muscle cells in vitro, the compounds of Examples 1, 4, 20, 22, 27, 31, 36, 50, 52, and 58 were tested using A7r5 cells derived from the aorta of a rat (ATCC-CRL-1444).

Using DMEM medium containing 10% FBS, the cells were placed on 96-well microtiter plates with 5×10$^3$ cells/0.2 ml/well and then incubated. The medium was exchanged for 2% FBS-containing DMEM medium on the third day and then for 0.2% FBS-containing DMEM medium on the fourth day from the start of the incubation. After 24-hour incubation in the 0.2% FBS-containing DMEM medium, the test compound was added. Each of the test compounds were added to the wells in the form of a solution or suspension in ethanol in an amount of 1 $\mu$l/well to final compound concentrations indicated in Table 3 below and the resultant ethanol concentration of 0.5% in each well. After additional 24-hour incubation, the medium was removed, and 0.2 ml of DMEM medium and the test compound were added thereto again, and the cells were stimulated by serum (2% FBS). Forty-eight hours after the stimulation, the acid phosphatase activity in the wells was measured by means of a kit (Abacus Cell Proliferation Kit, available from Clontech Lab. Inc. CA, U.S.A.) and evaluated as an indication of cell proliferation. The results obtained are shown in Table 3 below.

TABLE 3

Inhibitory Effect on Proliferation
of Vascular Smooth Muscle Cells (3)

| | | Acid Phosphatase Activity | |
|---|---|---|---|
| Test Compound | Concn. ($\mu$M) | Absorbance (OD405 | % Control (%) |
| Control | | 0.867 ± 0.089 | 100 ± 10 |
| Example 1 | 10 | 0.727 ± 0.032 | 84 ± 4 |
| | 100 | 0.288 ± 0.073 | 33 ± 8 |
| Example 22 | 10 | 0.875 ± 0.013 | 101 ± 1 |
| | 100 | 0.777 ± 0.062 | 90 ± 7 |

TABLE 3-continued

Inhibitory Effect on Proliferation
of Vascular Smooth Muscle Cells (3)

| Test Compound | Concn. ($\mu$M) | Acid Phosphatase Activity | |
|---|---|---|---|
| | | Absorbance (OD405) | % Control (%) |
| Example 31 | 10 | 0.756 ± 0.025 | 87 ± 3 |
| | 100 | 0.600 ± 0.102 | 69 ± 12 |
| Example 36 | 10 | 0.733 ± 0.060 | 84 ± 7 |
| | 100 | 0.539 ± 0.055 | 62 ± 6 |
| Example 4 | 10 | 0.606 ± 0.020 | 70 ± 2 |
| | 30 | 0.062 ± 0.026 | 7 ± 3 |
| Example 20 | 10 | 0.472 ± 0.031 | 54 ± 4 |
| | 30 | 0.105 ± 0.027 | 12 ± 3 |
| Example 27 | 10 | 0.553 ± 0.033 | 64 ± 4 |
| | 30 | 0.225 ± 0.064 | 26 ± 7 |
| Example 50 | 10 | 0.699 ± 0.131 | 81 ± 15 |
| | 30 | 0.146 ± 0.026 | 17 ± 3 |
| Example 52 | 10 | 0.690 ± 0.071 | 80 ± 8 |
| | 30 | 0.043 ± 0.008 | 5 ± 1 |
| Example 58 | 10 | 0.417 ± 0.125 | 48 ± 14 |
| | 30 | 0.045 ± 0.006 | 5 ± 1 | n = 3,
Mean ± Standard Deviation

As is shown in Table 3, all the compounds tested inhibit the serum-stimulated proliferation of vascular smooth muscle cells.

Test Example 4

In Vivo Effect in Intimal Thickening Model (1)

In order to assess the inhibitory effect of the compound of the present invention on intimal thickening in vivo, the compound of Example 36 was tested using rabbit balloon injury models.

Cholesterol-fed rabbits in groups of eight (JW: CSK male, 11-week-old) were used to prepare rabbit balloon injury models. Briefly, rabbits were fed with a high cholesterol diet (cholesterol content: 1%) for 2 weeks before balloon treatment. The animals were balloon-treated with a balloon catheter (3 French, available from Baxter) under anesthesia to peel the aortic intima 5 times. The animals were orally administered with the compound which was suspended in a 1% carboxymethyl cellulose (CMC) solution (200 mg/kg). On the other hand, control animals were orally administered with a 1% CMC solution without the compound. The administrations were performed once a day from 1 week before the balloon treatment until the day before the dissection for evaluation.

After four weeks from the balloon treatment, specimens were taken from the aorta, stained with Elastica van Geison, and analyzed under an optical microscope. The image was processed to measure the thickness and area of the thickened intima. Averages of the thickness and area were obtained for each individual animal. The animals which died due to the operation and those having a serum cholesterol level of 3500 mg/dl or higher were excluded from the measurement. The number of animals used for the evaluation was 5 or 6 per group. The results obtained are shown in Table 4.

TABLE 4

Inhibitory Effect on Intimal
Thickening in Balloon Injury Models (1)

| | Control | Compound of Example 36 |
|---|---|---|
| Thickness of Intima ($\mu$m) | 103 ± 12 | 45 ± 31** |
| Area of Intima (mm$^2$) | 0.26 ± 0.03 | 0.11 ± 0.08** |

Means ± Standard Deviation;
**: P < 0.01

As shown in Table 4, the compound of Example 36 exhibits significant inhibitory effect on intimal thickening in the rabbit balloon injury intimal thickening models on both parameters of intimal thickness and intimal area.

Test Example 5

In Vivo Effect in Intimal Thickening Model (2)

In order to assess the inhibitory effect of the compound of the present invention on intimal thickening in vivo, the compound of Example 36 was tested using rabbit balloon injury models that were different from those used in Test Example 4 in week-age. Further, the effect was compared with that of Probucol which was reported to have an inhibitory effect on intimal thickening in balloon injury models (see *Proc. Natl. Acad. Sci. U.S.A.*, 89, pp 11312–11316 (1992)).

Cholesterol-fed rabbits in groups of seven (JW: CSK male, 15-week-old) were used to prepare rabbit balloon injury models. Briefly, rabbits were fed with a high cholesterol diet (cholesterol content: 1%) for 2 weeks before balloon treatment. The animals were balloon-treated with a balloon catheter (4 French, available from Baxter) under anesthesia to peel the aortic intima 5 times. The animals were orally administered with the compound which was suspended in a 1% CMC solution (200 mg/kg). On the other hand, control animals were orally administered with a 1% CMC solution without the compound. The administrations were performed once a day from 1 week before the balloon treatment until the day before the dissection for evaluation. In order to evaluate the degree of balloon injury, a balloon-nontreated group (3 animals) was prepared.

After four weeks from the balloon treatment, specimens were taken from the aorta, stained with Elastica van Geison, and analyzed under an optical microscope. The image was processed to measure the thickness and area of the thickened intima. Averages of the thickness and area were obtained for each individual animal. The animals which died after the operation and those having a serum cholesterol level of 3500 mg/dl or higher were excluded from the measurement. The number of animals used for the evaluation was 4 or 5 per group. The results obtained are shown in Table 5.

TABLE 5

Inhibitory Effect on Intimal
Thickening in Balloon Injury Models (2)

| | Control | Probucol | Compound of Example 36 | Balloon-nontreated |
|---|---|---|---|---|
| Thickness of Intima ($\mu$m) | 119 ± 19 | 92 ± 17 | 76 ± 16** | 46 ± 20** |

TABLE 5-continued

Inhibitory Effect on Intimal
Thickening in Balloon Injury Models (2)

| | Control | Probucol | Compound of Example 36 | Balloon-nontreated |
|---|---|---|---|---|
| Area of Intima (mm$^2$) | 1.32 ± 0.22 | 0.97 ± 0.28 | 0.81 ± 0.22* | 0.45 ± 0.21** |

Mean ± Standard Deviation;
*: P < 0.05;
**: P < 0.01

As can be seen from the results in Table 5, the compound of Example 36 exhibits significant inhibitory effect on intimal thickening in the rabbit balloon injury induced intimal thickening models on both parameters of intimal thickness and intimal area. The effect is higher than that of Probucol.

Industrial Applicability

The vascular intimal thickening inhibitory agent according to the present invention which comprises a 2,6-di-t-butylphenol derivative as an active ingredient shows a potent inhibitory action on cell proliferation caused by serum or PDGF in cultured vascular smooth muscle cells as well as a potent inhibitory effect on intimal thickening in balloon injury intimal thickening models. Therefore, the agent is useful for the treatment and prevention of restenosis due to vascular intimal thickening following PTCA.

What is claimed is:

1. A method for inhibiting proliferation of vascular smooth muscle cells, or for inhibiting thickening or vascular stenosis following percutaneous transluminal coronary angioplasty, comprising administering to a patient in need of said therapy an effective amount for said therapy of a compound of formula (1)

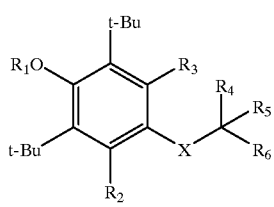

(1)

wherein X represents an oxygen atom or a group of formula

(2)

wherein n represents an integer of from 0 to 2;
$R_1$ represents a hydrogen atom or an acyl group;
$R_2$ represents a hydrogen atom, a lower alkyl group or a lower alkenyl group;
$R_3$ represents a lower alkyl group; and
$R_4$, $R_5$, and $R_6$, which may be the same or different, each represent a hydrogen atom, a substituted or unsubstituted alkyl group, a substituted or unsubstituted alkenyl group, a substituted or unsubstituted alkynyl group, or a substituted or unsubstituted aryl group; or
$R_3$ and $R_4$ may be taken together to form a 5-membered ring; or $R_5$ and $R_6$ may be taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzofuran ring, a benzo[b]thiophene ring, a benzo[b]thiophene-1-oxide ring or a benzo[b]thiophene-1,1-dioxide ring.

2. The method of claim 1, wherein
X is an oxygen atom;
$R_1$ is a hydrogen atom or an acyl group;
$R_2$ is a hydrogen atom, a lower alkyl group or a lower alkenyl group;
$R_3$ and $R_4$ are taken together to form a 5-membered ring; and
$R_5$ and $R_6$, which may be the same or different, each represent a hydrogen atom, a substituted or unsubstituted alkyl group, a substituted or unsubstituted alkenyl group, a substituted or unsubstituted alkynyl group, or a substituted or unsubstituted aryl group; or
$R_5$ and $R_6$ are taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzofuran ring.

3. The method of claim 1, wherein
X is an oxygen atom;
$R_1$ is a hydrogen atom or an acyl group;
$R_2$ is a hydrogen atom, a lower alkyl group or a lower alkenyl group;
$R_3$ and $R_4$ are taken together to form a 5-membered ring; and
$R_5$ and $R_6$, which may be the same or different, are each a substituted or unsubstituted alkyl group having 2 to 20 carbon atoms, a substituted or unsubstituted alkenyl group having 2 to 20 carbon atoms, a substituted or unsubstituted alkynyl group having 2 to 20 carbon atoms, or a substituted or unsubstituted aryl group; or
$R_5$ and $R_6$ are taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzofuran ring.

4. The method of claim 1, wherein
X is an oxygen atom;
$R_1$ is a hydrogen atom;
$R_2$ is a hydrogen atom;
$R_3$ and $R_4$ are taken together to form a 5-membered ring; and
$R_5$ and $R_6$, which may be the same or different, are each a substituted or unsubstituted alkyl group having 2 to 20 carbon atoms, a substituted or unsubstituted alkenyl group having 2 to 20 carbon atoms, a substituted or unsubstituted alkynyl group having 2 to 20 carbon atoms, or a substituted or unsubstituted aryl group; or
$R_5$ and $R_6$ are taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and R4 are taken together to form a benzofuran ring.

5. The method of claim 1, wherein

X is an oxygen atom;

$R_1$ is a hydrogen atom;

$R_2$ is a hydrogen atom;

$R_3$ and $R_4$ are taken together to form a 5-membered ring; and $R_5$ and $R_6$, which may be the same or different, are each a substituted or unsubstituted alkyl group having 2 to 20 carbon atoms or a substituted or unsubstituted alkenyl group having 2 to 20 carbon atoms; or $R_5$ and $R_6$ are taken together to form a cycloalkyl group provided that $R_6$ is nil when $R_3$ and $R_4$ are taken together to form a benzofuran ring.

6. The method of claim 1, wherein said compound is selected from the group consisting of 4,6-di-t-butyl-2,2-di-n-butyl-5-hydroxy-2,3-dihydrobenzofuran, 4,6-di-t-butyl-5-hydroxy-2,3-dihydrobenzofuran-2-spiro-1'-cyclohexane, 4,6-di-t-butyl-5-hydroxy-2,3-dihydrobenzofuran-2-spiro-1'-cycloheptane, 4,6-di-t-butyl-5-hydroxy-2,3-dihydrobenzofuran-2-spiro-1'-cyclooctane, 4,6-di-t-butyl-2,2-di-n-pentyl-5-hydroxy-2,3-dihydrobenzofuran, 4,6-di-t-butyl-2,2-di-n-hexyl-5-hydroxy-2,3-dihydrobenzofuran, and 2,2-di-i-amyl-4,6-di-t-butyl-5-hydroxy-2,3-dihydrobenzofuran.

7. The method of claim 1, wherein said compound is 4,6-di-t-butyl-2,2-di-n-pentyl-5-hydroxy-2,3-dihydrobenzofuran.

8. The method of claim 1, wherein

X is a group of formula (2):

(2)

wherein n is an integer of from 0 to 2;

$R_1$ is a hydrogen atom or an acyl group;

$R_2$ is a hydrogen atom, a lower alkyl group or a lower alkenyl group;

$R_3$ and $R_4$ are taken together to form a 5-membered ring; and $R_5$ and $R_6$, which may be the same or different, are each a hydrogen atom, a substituted or unsubstituted alkyl group, a substituted or unsubstituted alkenyl group, a substituted or unsubstituted alkynyl group, or a substituted or unsubstituted aryl group; or $R_5$ and $R_6$ are taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzo[b]thiophene ring, a benzo[b]thiophene-1-oxide ring or a benzo[b]thiophene-1,1-dioxide ring.

9. The method of claim 1, wherein

X is a sulfur atom;

$R_1$ is a hydrogen atom or an acyl group;

$R_2$ is a hydrogen atom, a lower alkyl group or a lower alkenyl group;

$R_3$ and $R_4$ are taken together to form a 5-membered ring; and $R_5$ and $R_6$, which may be the same or different, are each a hydrogen atom, a substituted or unsubstituted alkyl group, a substituted or unsubstituted alkenyl group, a substituted or unsubstituted alkynyl group, or a substituted or unsubstituted aryl group; or $R_5$ and $R_6$ are taken together to form a cycloalkyl group or a heterocyclic ring derived from a cycloalkyl group by substituting any one or more methylene groups on the ring with oxygen atoms, sulfur atoms or alkyl-substituted nitrogen atoms;

provided that $R_6$ is nil when $R_3$ and $R_4$ are taken together to form a benzo[b]thiophene ring.

10. The method of claim 1, wherein

X is a sulfur atom;

$R_1$ is a hydrogen atom or an acyl group;

$R_2$ is a hydrogen atom, a lower alkyl group or a lower alkenyl group;

$R_3$ and $R_4$ are taken together to form a 5-membered ring; and $R_5$ and $R_6$, which may be the same or different, are each a hydrogen atom, a substituted or unsubstituted alkyl group or a substituted or unsubstituted alkenyl group; or $R_5$ and $R_6$ are taken together to form a cycloalkyl group;

provided that $R_6$ is nil when $R_3$ and $R_4$ are taken together to form a benzo[b]thiophene ring.

11. The method of claim 1, wherein

X is a sulfur atom;

$R_1$ is a hydrogen atom;

$R_2$ is a hydrogen atom;

$R_3$ and $R_4$ are taken together to form a 5-membered ring; and $R_5$ and $R_6$, which may be the same or different, are each a substituted or unsubstituted alkyl group or a substituted or unsubstituted alkenyl group; or $R_5$ and $R_6$ are taken together to form a cycloalkyl group;

provided that $R_6$ is nil when R3 and $R_4$ are taken together to form a benzo[b]thiophene ring.

12. The method of claim 1, wherein said compound is selected from the group consisting of 4,6-di-t-butyl-5-hydroxy-2,2-di-n-pentyl-2,3-dihydrobenzothiophene, 4,6-di-t-butyl-5-hydroxy-2,2-di-n-butyl-2,3-dihydrobenzothiophene, 4,6-di-t-butyl-5-hydroxy-2,2-di-i-amyl-2,3-dihydrobenzothiophene, 4,6-di-t-butyl-5-hydroxy-2,2-di-n-hexyl-2,3-dihydrobenzothiophene, 4,6-di-t-butyl-5-hydroxy-2,3-dihydrobenzothiophene-2-spiro-11-cyclohexane, 4,6-di-t-butyl-5-hydroxy-2,3-dihydrobenzothiophene-2-spiro-1'-cycloheptane, and 4,6-di-t-butyl-5-hydroxy-2,3-dihydrobenzothiophene-2-spiro-1'-cyclooctane.

13. The method of claim 1, wherein said compound is 4,6-di-t-butyl-5-hydroxy-2,2-di-n-pentyl-2,3-dihydrobenzothiophene.

14. The method according to claim 1, wherein said patient is one in need of inhibition of restenosis in the coronary artery which occurs after percutaneous transluminal coronary angioplasty.

15. The method according to claim 1, wherein said compound is administered along with a physiologically non-toxic solid or liquid pharmaceutical carrier, in a dosage form selected from the group consisting of tablets, granules, pills, capsules, solutions, syrups, suspensions, emulsions and injectable solutions.

16. The method of claim 1, wherein said compound is administered orally.

17. The method according to claim 1, wherein said compound is administered parenterally.

18. The method of claim 1, wherein said compound is administered by intravenous injection.

19. The method of claim 1, wherein administration is by sustained release.

20. The method according to claim 1, wherein administration of said compound is through a catheter.

21. The method of claim 1, wherein said effective amount is in the range of 100 to 300 mg per day.

22. The method of claim 21, wherein said compound is administered one to three times per day.

23. The method according to claim 1, wherein said administration is begun prior to balloon percutaneous transluminal coronary angioplasty, said method further comprising then treating said patient with percutaneous transluminal coronary angioplasty.

24. The method according to claim 23, wherein said administration is continued after said percutaneous transluminal coronary angioplasty.

25. The method according to claim 1, wherein, prior to said administration, said patient is treated with percutaneous transluminal coronary angioplasty.

\* \* \* \* \*